United States Patent [19]

DeVries et al.

[11] Patent Number: 4,670,421

[45] Date of Patent: Jun. 2, 1987

[54] ANTIATHEROSCLEROTIC SILANES

[75] Inventors: Vern G. DeVries, Ridgewood, N.J.; Janis Upeslacis, Pomona, N.Y.

[73] Assignee: American Cyanamid Company, Stamford, Conn.

[21] Appl. No.: 397,001

[22] Filed: Jul. 12, 1982

[51] Int. Cl.[4] .................. A61K 31/695; C07F 7/10
[52] U.S. Cl. ................................. 514/63; 556/418; 556/419; 548/110; 546/14; 549/215
[58] Field of Search ............. 556/418, 419; 424/184; 548/110; 546/14; 514/63; 549/215

[56] References Cited

U.S. PATENT DOCUMENTS

| | | | |
|---|---|---|---|
| 2,789,122 | 4/1957 | Cason et al. | 556/418 |
| 3,513,184 | 5/1970 | Brison et al. | 556/418 |
| 3,853,935 | 12/1974 | Roshdy et al. | 556/418 |

Primary Examiner—Paul F. Shaver
Attorney, Agent, or Firm—Edward A. Conroy, Jr.

[57] ABSTRACT

This invention is concerned with novel 4-[(trialkylsilyl)alkylamino]phenyl compounds and their use as antiatherosclerotic agents.

19 Claims, No Drawings

ANTIATHEROSCLEROTIC SILANES

BACKGROUND OF THE INVENTION

This invention relates to new organic compounds useful as pharmaceutical agents. The novel silanes of the present invention are antiatherosclerotic agents capable of ameliorating atherosclerosis by counteracting the formation or development of atheromatous lesions in the arterial wall of mammals. The invention also relates to the chemical synthesis of the novel compounds disclosed herein. In addition, the invention pertains to novel pharmaceutical compositions for the utilization of these compounds in the treatment of disease in mammals. Further, the invention contemplates methods for treating atherosclerosis in a manner designed to prevent, arrest, or reverse the course of the disease.

Atherosclerosis is a form of arteriosclerosis characterized by lipid accumulation in and thickening of the arterial walls of both medium and large-sized arteries. Arterial walls are thereby weakened and the elasticity and effective internal size of the artery is decreased. Atherosclerosis is the most common cause of coronary artery disease and is of great medical importance since the occlusion of medium and large-sized arteries diminishes the supply of blood to vital organs such as the heart muscles and the brain. The sequelae to atherosclerosis include ischemic heart disease, heart failure, life-threatening arrhythmias, senility, and stroke.

The evidence that hyperlipidemia is one of the factors involved in coronary artery disease is very impressive. A most important study carried out in Framingham, Mass. (Gordon and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis, et al., 1974).

We have now found that certain silanes can safely and effectively lower both serum lipids in warm-blooded animals. Such action on serum lipids is considered to be very useful in the treatment of atherosclerosis. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease and to stroke.

The fact that cholesterol is a major component of atherosclerotic lesions of plaques has been known for more than 100 years. Various researchers have studied the role of cholesterol in lesion formation and development and also, more importantly, whether lesion formation can be prevented or lesion development arrested or reversed. Atheromatous lesions have now been shown [Adams, et al., Atherosclerosis, 13, 429 (1974)] to contain a greater quantity of esterified as opposed to unesterified cholesterol than the surrounding undiseased arterial wall. The intracellular esterification of cholesterol with fatty acids is catalyzed by the enzyme Fatty acyl CoA:cholesterol acyl transferase of ACAT and the accumulation and storage of cholesteryl esters in the arterial wall is associated with increased activity of this enzyme [Hashiomoto and Dayton, Atherosclerosis, 28, 447 (1977)]. In addition, cholesteryl esters are removed from cells at a slower rate than unesterified cholesterol [Bondjers and Bjorkerud, Atherosclerosis, 15, 273 (1972) and 22, 379 (1975)]. Thus, inhibition of the ACAT enzyme would diminish the rate of cholesterol esterification, decrease the accumulation and storage of cholesteryl esters in the arterial wall, and prevent or inhibit the formation and development of athermatous lesions. The compounds of the present invention are very potent inhibitors of the ACAT enzyme. Thus, these compounds are useful for controlling and reducing the cholesteryl ester content of mammalian arterial walls, and decreasing the accumulation and storage of cholesterol in the arterial walls of mammals. Further, the compounds of this invention inhibit the formation or development of atherosclerotic lesions in mammals.

The compounds of this invention exhibit antiatherosclerotic activity and the invention should not be construed as limited to any particular mechanism of antiatherosclerotic action.

U.S. Pat. Nos. 4,000,265, 4,296,240 and 4,297,349 are cited to show the state of the art.

SUMMARY OF THE INVENTION

This invention relates to new silanes, their preparation, pharmaceutical compositions containing them, and their use in the treatment of atherosclerosis. More particularly, it is concerned with silanes which may be represented by Formula I:

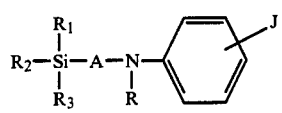

wherein A represents a saturated or unsaturated alkylene moiety of 3 to 20 carbon atoms which may be branched or unbranched and which may contain a saturated or unsaturated cycloalkyl group; $R_1$, $R_2$, and $R_3$ may be the same or different and are independently selected from the group consisting of $C_1$–$C_6$ alkyl, $C_2$–$C_6$ alkenyl, $C_2$–$C_6$ alkynyl, $C_4$–$C_7$ cycloalkyl, and $C_4$–$C_{20}$ cycloalkylalkyl; R is selected from the group consisting of hydrogen or a group convertible in vivo thereinto such as methyl, carboxymethyl, acetyl, succinyl, and 1-(sodiumsulfo)-$C_1$-$C_4$-alkyl; and (a) J is

Z being selected from the group consisting of hydrogen, $C_1$–$C_4$ alkyl, hydroxy, $C_1$–$C_4$ alkoxy, ($C_1$–$C_4$ alkoxy)-$C_1$–$C_4$ alkoxy, di-($C_1$–$C_4$-alkyl)-$C_1$–$C_4$-alkoxy, 2,3-dihydroxypropyl, allyloxy, 2,3-epoxypropyl, benzyloxy, phenoxy, 3-pyridyloxy, pyridylmethoxy, tetrahydropyranyloxy, amino, ($C_1$–$C_4$-alkyl)amino, di-($C_1$–$C_4$ alkyl)amino, allylamino, propargylamino, 2-sulfoethylamino, ($C_1$–$C_4$-alkanoyl)amino, benzoylamino, ($C_1$–$C_4$-alkanesulfonyl)amino, benzenesulfonylamino, toluenesulfonylamino; (b) J is (carboxy)$C_1$–$C_4$ alkyl, (carboxy)$C_2$–$C_4$-alkenyl, (carboxy)$C_2$–$C_4$-alkynyl, ($C_1$–$C_4$-carboalkoxy)-$C_1$–$C_4$-alkyl, ($C_1$–$C_4$-carboalkoxy)-$C_2$–$C_4$-alkenyl, ($C_1$–$C_4$-carboalkoxy)-$C_2$–$C_4$-alkynyl; and the pharmaceutically acceptable, non-toxic, acid-addition and cationic salts thereof.

This invention also relates to a method of treating atherosclerosis in mammals which comprises administering to said mammal an effective amount of a compound as recited above.

This invention also relates to a method of treating hyperlipidemia in mammals which comprises administering to said mammal an effective amount of a compound as recited above.

This invention also relates to a method of reducing the cholesterol content of the arterial walls of mammals which comprises administering to said mammal an effective amount of a compound as recited above.

This invention further relates to a method of inhibiting atherosclerotic lesion development in mammals which comprises administering to said mammal an effective amount of a compound as recited above.

This invention still further relates to a pharmaceutical composition which comprises an effective antiatherosclerotic amount of a compound as recited above in association with a pharmaceutically acceptable carrier.

Finally, this invention relates to processes for preparing compounds as recited above.

Preferred embodiments of the invention involve compounds of Formula I wherein R is hydrogen and J is

More preferred embodiments of the invention involve compounds of Formula I wherein R is hydrogen, J is

and A represents a saturated or unsaturated alkylene moiety of 3 to 20 carbon atoms. Even more preferred embodiments involve compounds of Formula I wherein R is hydrogen, J is

Z is hydroxy or loweralkoxy, A represents a saturated alkylene moiety of 3 to 20 carbon atoms, and $R_1$, $R_2$, and $R_3$ are selected from the group consisting of $C_1$–$C_4$ alkyl, and the pharmaceutically acceptable, non-toxic, acid addition and cationic salts thereof. The most preferred embodiments involve compounds of Formula I wherein R is hydrogen, J is

Z is hydroxy or $C_1$–$C_4$ alkoxy, A represents a saturated alkylene moiety of 3–20 carbon atoms. and $R_1$, $R_2$, and $R_3$ are all methyl, and the pharmaceutically acceptable, non-toxic acid addition and cationic salts thereof.

Preferred specific embodiments involve the compounds:

Ethyl 4-[11-(trimethylsilyl)undecylamino]benzoate
4-[11-Trimethylsilyl)undecylamino]benzoic acid
Sodium 4-[11-(trimethylsilyl)undecylamino]benzoate
Ethyl 4-[14-(trimethylsilyl)tetradecylamino]benzoate
4-[14-(Trimethylsilyl)tetradecylamino]benzoic acid
sodium 4-[14-(trimethylsilyl)tetradecylamino]benzoate
Ethyl 4-[3-(trimethylsilyl)propylamino]benzoate
4-[3-(Trimethylsilyl)propylamino]benzoic acid
Sodium 4-[3-(trimethylsilyl)propylamino]benzoate

DETAILED DESCRIPTION OF THE INVENTION

The compounds of this invention are, in general, white crystalline solids having characteristic melting points and spectra. They are soluble in organic solvents such as alcohol, chloroform, toluene, dimethylformamide, and the like; but not generally very soluble in water. Those compounds which are organic bases may be converted to their non-toxic, acid-addition salts with a variety of pharmaceutically acceptable organic and inorganic acids. Thus, salts may be formed by admixture of the organic base in a neutral solvent with an acid such as sulfuric, phosphoric, hydrochloric, trifluoroacetic, citric, tartaric, ascorbic, and the like.

The novel compounds of the present invention in their acidic forms or those which contain acidic substituents are converted to their organic or inorganic cationic salts for therapeutic use. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

Many of the (trialkylsilyl)alkyl halides required as intermediates for the synthesis of the novel 4-[(trialkylsilyl)alkylamino]phenyl compounds of the present invention are prepared by the dilithium copper tetrachloride-catalyzed coupling of (trialkylsilyl)alkyl magnesium halide with an appropriate α,ω-dihaloalkanes, for example, reaction of 3-(trimethylsilyl)propyl magnesium bromide and 1,8-dibromooctane in the presence of dilithium copper tetrachloride affords 11-(trimethylsilyl)undecyl bromide. (Trimethylsilyl)alkanoic acids are similarly prepared by reacting (trialkylsilyl)alkyl magnesium halides with magnesium salts of ω-haloalkanoic acids in the presence of dilithium copper tetrachloride, for example, reactions of 11-bromoundecanoic acid with methyl magnesium bromide followed by 3-(trimethylsilyl)propyl magnesium bromide and dilithium copper tetrachloride yields 14-(trimethylsilyl)tetradecanoic acid. Alternatively, the (trialkylsilyl)alkyl halides or (trialkylsilyl)alkanoic acids can be prepared from reaction of trialkylsilyl magnesium halides with the appropriate α,ω-dihaloalkanes or magnesium ω-haloalkanoic acids. Certain of the (trialkylsilyl)alkanoic acids are converted to their corresponding acyl chlorides with for example thionyl chloride and reacted with appropriate arylamines to form amides; others are reduced with diborane or metal hydrides to the corresponding alcohols, as for example reduction of 14-(trimethylsilyl)tetradecanoic acid with diborane affords 14-(trimethylsilyl)tetradecanol. The alcohols are converted to the corresponding bromides with hydrogen bromide or phosphorus tribromide, as for example the conversion of 3-(trimethylsilyl)propanol to 3-(trimethylsilyl)propyl bromide with phosphorus tribromide, or alternatively reacted with methanesulfonyl chloride to yield O-methanesulfonates, as exemplified by the conversion of 14-(trimethylsilyl)tetradecanol to 1-(methanesulfonyloxy)-14-(trimethylsilyl)tetradecane.

Many of the novel 4-(trialkylsilylalkylamino)phenyl compounds of the present invention may be prepared by reaction of the appropriate 4-aminophenyl compound with a suitable alkylating agent such as an alkyl halide, sulfate, tosylate, or trifluoromethanesulfonate with or without a solvent at 30° C. to 150° C. Appropriate 4-aminophenyl compounds are, for example, ethyl 4-aminobenzoate; 2,3-dihydroxypropyl 4-amino-benzoate; phenyl 4-aminobenzoate; 1-(4-aminobenzoyl)pyrrolidine; and ethyl 4-(4-aminophenyl)butyrate. Suitable solvents are loweralkanols, N,N-dimethylformamide, N,N-dimethylacetamide, 1,2-dimethoxyethane, acetonitrile, toluene, benzene, hexamethylphosphoramide and the like. The reaction may be carried out with two equivalents of the 4-aminophenyl compound or with one equivalent of the compound plus one equivalent of a base such as an alkali carbonate or bicarbonate or an unreactive organic base such as diisopropylethylamine or alternatively with a catalytic amount of copper powder when an alkyl halide is used as the alkylating agent. Similarly, alkylation of the sodium salt (formed with sodium hydride) of either the amino group of a 4-aminophenyl compound or the anilide moiety of a 4-(acetylamino)phenyl compound yields the novel 4-(trialkylsilylalkylamino)phenyl compounds or an N-acetyl derivative thereof. Removal of the N-acetyl group by conventional hydrolytic methods affords the desired 4-(trialkylsilylalkylamino)phenyl compounds.

Alternative methods of preparation of these compounds are by reductive alkylation of a 4-aminophenyl compound, which may be generated in situ by reduction of a 4-aminophenyl precursor such as a 4-nitrophenyl compound and the like or by a metal hydride reduction of a 4-(acylamino)phenyl compound. For example, 14-(trimethylsilyl)tetradecanal or another carbonylalkane and 4-aminobenzoic acid are reduced under 1–10 atmospheres of hydrogen using an activated metal catalyst or with a metal hydride such as sodium borohydride forming 4-[14-(trimethylsilyl)tetradecylamino]benzoic acid and the like. Diborane reduction of 4-(trialkylsilylalkanoylamino)phenyl compounds such as ethyl 4-[14-(trimethylsilyl)tetradecanoylamino]benzoate at room temperature or above for 1–6 hours yields the corresponding 4-(trialkylsilylalkylamino)phenyl compounds such as ethyl 4-[14-(trimethylsilyl)tetradecylamino]benzoate. The 4-(trialkylsilylalkanoylamino)phenyl compounds used in these reductions are prepared by acylation of the appropriate 4-aminophenyl compounds with suitable acylating agents, such as trialkylsilylalkanoyl halides. To prepare for example the 4-(trialkylsilylalkylamino)phenyl alkenoic and alkynoic acids it is advantageous to form the corresponding trialkylsilylalkylchloroimide from the 4-(trialkylsilylalkanoylamino)phenyl compounds using phosphorus oxychloride and base, and then reduce the trialkylsilylalkylchloroimide moiety to a trialkylsilylalkylamino group with sodium borohydride.

A method useful for the introduction of the trialkylsilylalkylamino group into aromatic compounds is nucleophilic aromatic substitution. An example of this method is the reaction of 14-(trimethylsilyl)tetradecylamine (or the anion derived therefrom by treatment with a strong base) with ethyl 4-fluorobenzoate to yield ethyl 4-[14-(trimethylsilyl)tetradecylaminobenzoate. In certain instances an amine such as 14-(trimethylsilyl)tetradecylamine may be reacted with a benzyne such as that derived from ethyl 4-bromobenzoate by treatment with sodium amide to yield the 4-(trialkylsilylalkylamino)phenyl compound, in this case ethyl 4-[14-(trimethylsilyl)tetradecylamino]benzoate.

The 4-(trialkylsilylalkylamino)benzoic, benzoylalkanoic, and phenylalkanoic acids of this invention are often prepared from the corresponding 4-aminobenzoic, benzoylalkanoic, and phenylalkanoic acids by the sequence involving esterification of the amine-acid with ethanol in the presence of boron trifluoride etherate, followed by alkylation of the amino function by the methods above. The free acids are then liberated by hydrolysis of the ester with aqueous alcoholic sodium hydroxide at 80° for 2–10 hours followed by acidification. The acids obtained by this procedure may be converted to the corresponding metallic cationic salts. For example, the sodium salt may be prepared by reaction of the acid with sodium hydroxide in a mixture of ethanol and water.

Alternatively, the acids of this invention may be prepared by hydrolysis of the corresponding nitriles or various amides, imidates or oxazolines. The carboxylic acid moiety may also be generated by oxidation of the corresponding aldehydes, acetophenones, benzyl alcohols, or toluenes, most often with the use of an amine-protecting group such as trifluoroacetyl or t-butyloxycarbonyl.

The carboxaldehydes of this invention may be prepared by several methods among which is alkylation of the corresponding acetal by the methods above followed by hydrolysis of the resulting 4-(trialkylsilylalkylamino)phenyl acetal to the desired aldehyde. Aldehydes may also be prepared by reduction of the appropriate nitriles. For example, treatment of 4-[14-(trimethylsilyl)tetradecylamino]benzonitrile with stannic chloride and anhydrous hydrogen chloride gas, followed by hydrolysis in hot water provides 4-[14-(trimethylsilyl)tetradecylamino]benzaldehyde. These reductions are also conveniently carried out with hydrides such as diisobutyl aluminum hydride.

The novel esters and amides of the present invention may readily be prepared by treating a derivative of the corresponding carboxylic acid, such as the acid halide, mixed acid anhydride or activated ester or amide with the appropriate alcohol or amine, respectively. These reactions may be carried out in an inert solvent at a temperature of 50°–125° C. for 30 minutes to 18 hours or more. In the case of the acid halide and other acid-forming acylating agents, the reaction is carried out in the presence of an acid scavenger such as diisopropylethylamine; 4-dimethylaminopyridine; pyridine; triethylamine; finely powdered sodium carbonate and the like. A protecting group on the amino nitrogen is used for best results. The simplest protecting group is provided by protonation of the amine to yield an anilinium salt prior to or during formation of the acylating from of the carboxyl group. Acylation of the amino group by carefully selected acyl groups such as carbobenzyloxy, carbo-t-butoxy, and trifluoroacetyl provides protection of this group from self-acylation during amine or ester formation. These protecting groups are then removed by catalytic hydrogenation, mild acid treatment, and mild alkali treatment, respectively. Other N-acyl protecting groups such as acetyl and succinoyl may be used and these are removed by conventional methods. Activated esters and amides, useful to synthesize the esters and amides of the present invention, are those containing carboxymethyl, 4-nitrophenyl, N-oxysuccinimide and 1-imidazolyl groups and the like. In certain cases, treatment of the acids with an excess of an appropriate hydroxy-containing substrate in the presence of a Lewis or mineral acid such as boron trifluoride, sulfuric acid or hydrochloric acid affords the corresponding esters. Ordinary esters such as the methyl and ethyl esters are sufficiently reactive to form the amides of the 4-(trialkylsilylalkylamino)benzoic acids and highly reactive amine substrates such as hydroxylamine, hydrazines and certain alkyl primary amines. With certain kinds of substrates in order to form amides it is necessary to first form the alkali metal or strong organic base salts of these substrates prior to reacting them with the various aforementioned acylating forms of the 4-(trialkylsilylalkylamino)benzoic acids. For example, the aminoalkanecarboxylic and aminoalkanesulfonic acids are zwitterionic and must be converted to their salts, suitably in situ. They may also be used in the form of their esters and then hydrolyzed after amide formation. Certain substrates which are neutral, like the carboxamides, or slightly acidic, like the alkane or arene sulfonamides, are converted to reactive sodium salts by reaction with sodium hydride or other basic reagents.

The α-substituted 4-(trialkylsilylalkylamino)acetophenones of the invention are prepared by reaction of a derivative of the appropriate benzoic acid, such as 4-[14-(trimethylsilyl)tetradecylamino]benzoyl chloride hydrochloride, with two or more equivalents of the reactive salt of an acidic methylene compound, for example the sodium salt of diethyl malonate. Other benzoic acid derivatives are also suitable for this reaction, such as 4-[N-trifluoroacetyl(trialkylsilylalkyl)amino]benzoyl chloride, a 4-[N-tert-butyloxycarbonyl(trialkylsilylalkylamino]benzoyl chloride or a methyl 4-(trialkylsilylalkylamino)benzoate ester. In some cases the final step in the preparation of the α-substituted 4-(trialkylsilylalkylamino)acetophenones is the removal of the nitrogen-protecting group. In other cases, hydrolysis of one or more of the ester groups in the acylation product affords an unstable polycarboxylic acid which undergoes decarboxylation to allow the preparation of another acetophenone derivative. For example, the reaction of tert-butyl ethyl 4-[14-(trimethylsilyl)tetradecylamino]benzoylmalonate with trifluoroacetic acid affords ethyl 4-[14-(trimethylsilyl)tetradecylamino]benzoylacetate. In other bases, hydrolysis of one or more of the ester groups allows the preparation of the corresponding acid derivative. For example, the hydrolysis of ethyl 4-[14-(trimethylsilyl)tetradecylamino]benzoylacetate yields 4-[14-(trimethylsilyl)tetradecylamino]benzoylacetic acid.

An alternative procedure for preparing certain α-substituted-4-(trialkylsilylalkylamino)acetophenones is alkylation of the corresponding 4-aminoacetophenone by the methods above. For example, alkylation of methyl 3-(4-aminobenzoyl)propionate with 14-(trimethylsilyl)tetradecyl bromide yields methyl 3-(4-[14-(trimethylsilyl)tetradecylamino]benzoyl)propionate. The related carboxylic acids are then obtained by hydrolysis. Certain of these acids are particularly useful for the preparation of [4-(trialkylsilylalkylamino)phenyl]alkanoic acids by reduction. For example, the Clemmensen or Wolff-Kishner reduction of 3-[4-[14-(trimethylsilyl)tetradecylamino]benzoyl]propionic acid yields 4-[4-[14-(trimethylsilyl)tetradecylamino]phenyl]butyric acid.

The [4-(trialkylsilylalkylamino)phenyl]alkenoic acids may be prepared by condensation of the appropriate aldehydes or by dehydration of the corresponding substituted-phenyl-hydroxyalkanoic acids. For example, ethyl 5-[4-[14-(trimethylsilyl)tetradecylamino]phenyl]-2,4-pentadienoate is obtained by the Wittig reaction of 4-[14-(trimethylsilyl)tetradecylamino]benzaldehyde with the Wittig reagent, triethyl 4-phosphonocrotonate. Alternatively, these alkenoic acids are obtained by heating 4-[N-trialkylsilylalkyl-N-(methyl or acetyl)amino]benzaldehydes with the sodium salt of the carbanion of ethyl acetate or with a mixture of ethyl acetate, acetic anhydride and potassium acetate. The second method is illustrated by dehydration of ethyl 3-[4-[14-(trimethylsilyl)tetradecylamino]phenyl]-3-hydroxypropionate to yield ethyl 4-[14-(trimethylsilyl)tetradecylamino]cinnamate.

The acetylenic analogs are prepared by dehydrobromination of the side-chain vic-dibrominated alkanoic acids. For example, dehydrobromination of ethyl 3-[4-[14-(trimethylsilyl)tetradecylamino]phenyl]-2,3-dibromopropionate yields ethyl 3-[4-[14-(trimethylsilyl)tetradecylamino]phenyl]propiolate. The acetylenic acids are also formed from 4-(trialkylsilylalkylamino)phenylacetylene metal salts by carboxylation with carbon dioxide. The 4-(trialkylsilylalkylamino)phenylacetylenes are also used by N-acylating with t-butyl azidoformate followed by conversion to the lithium acetylide salt and subsequent reaction of the lithium salt with boron trifluoride etherate in tetrahydrofuran at −20° C. to form tris-[4-(trialkylsilylalkylamino)phenylethynyl]boranes. The tetrahydrofuran solution of the borane is in turn reacted with ethyl diazoacetate, followed by water to yield ethyl 4-[4-(trialkylsilylalkylamino)phenyl]butynoate.

The 4-(trialkylsilylalkylamino)phenylalkanoic acids, amides, or esters are also prepared by catalytic reduction at 1 to 10 atmospheres of hydrogen of the corresponding alkanoic or alkynoic derivatives.

The 4-(trialkylsilylalkylamino)phenylalkanoic acids and derivatives are prepared by Friedel-Crafts acylation of the N-acyl-N-alkylanilines with the appropriate dicarboxylic acid anhydride or half acid chloride. The 4-(trialkylsilylalkylamino)benzoylalkanoic acids or esters, obtained by this and by other syntheses, may be converted to the 4-(trialkylsilylalkylamino)phenylalkanoic acids by reduction with (a) hydrazine and alkali in diethylene glycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of the 4-(trialkylsilylalkylamino)phenylalkanoic acids are prepared by heating the corresponding 4-(trialkylsilylalkylamino)phenyl alkyl ketones with aqueous alcoholic ammonium polysulfide followed by hydrolysis to yield the acids with the same number of carbon atoms as the ketone. These acids are also prepared by reacting 4-(N-t-butyloxycarbonyl-N-trialkylsilylalkylamino)phenylmagnesium halides with 2-(3-halopropyl)-2-oxazolines, followed by mild acid removal of 2-oxazolinyl and t-butoxycarbonyl protecting groups. Similarly, the above Grignard reagent can be reacted with 3-bromo-triethylorthopropionate in the presence of dilithiumtetrachlorocuprate to yield the desired acids after removal of the protecting groups from the amino and carboxyl groups.

The preparation and properties of the compounds of this invention will be described in greater detail in conjunction with the specific examples shown below.

The compounds of the present invention were assayed for two types of biological activity related to their potential use as antiatherosclerotic agents. Compounds were tested in vitro for their ability to inhibit the enzymes fatty acyl CoA:cholesterol acyl transferase (ACAT) and in vivo for serum hypolipidemic activity as measured by their ability to inhibit lipid absorption in rats. The compounds were tested for their ability to inhibit ACAT according to the following procedure:

Rat adrenals were homogenized in 0.2M monobasic potassium phosphate buffer, pH 7.4, and centrifuged at 1000 times gravity for 15 minutes at 5° C. The supernatant, containing the microsomal fraction, served as the source of the cholesterol-esterifying enzyme, fatty acyl CoA:cholesterol acyl transferase (ACAT). A mixture comprising 50 parts of adrenal supernatant, 10 parts of albumin (BSA) (50 mg./ml.), 3 parts of test compound (final concentration 5.2 µg./ml.) and 500 parts of buffer was preincubated at 37° C. for 10 minutes. After treatment with 20 parts of oleoyl CoA($^{14}$C-0.4 µCi) the mixture was incubated at 37° C. for 10 minutes. A control mixture, omitting the test compound, was prepared and treated in the same manner. The lipids from the incubation mixture were extracted into an organic solvent and separated by thin-layer chromatography. The cholesteryl ester fraction was counted in a scintillation counter. This procedure is a modification of that described by Hashimoto, et al., Life Scie., 12 (Part II), 1-12 (1973).

The results of this test on representative compounds of this invention appear in Table I.

TABLE I

| Compound | % Inhibition |
|---|---|
| Ethyl 4-[11-(trimethylsilyl)undecylamino]benzoate | 17 |
| 4-[11-Trimethylsilyl)undecylamino]benzoic acid | 57 |
| Sodium 4-[11-(trimethylsilyl)undecylamino]benzoate | 56 |
| Ethyl 4-[14-(trimethylsilyl)tetradecylamino]benzoate | 50 |
| 4-[14-(Trimethylsilyl)tetradecylaminobenzoic acid | 60 |
| Sodium 4-[14-(trimethylsilyl)tetradecylamino]benzoate | 62 |
| Ethyl 4-[3-(trimethylsilyl)propylamino]benzoate | 59 |
| 4-[3-(Trimethylsilyl)propylamino]benzoic acid | 12 |
| Sodium 4-[3-(trimethylsilyl)propylamino]benzoate | 23 |

The compounds were also tested for their ability to lower lipid levels in mammals. The compounds were administered orally admixed with diet (0.1% by weight) to groups of four male rats COBS, CD, SD strain from Charles River Breeding Laboratories, Inc, Wilmington, Mass. A control group of eight rats was maintained on the diet alone; test groups were maintained on the diet plus 0.1% of test compounds by weight. After 5 days treatment, serum cholesterol and triglyceride concentrations were determined by direct enzymatic procedures using a Centrifichem ® System 400 autoanalyzer (Union Carbide Co.). Cholesterol concentrations were determined by the combined cholesterol esterase-cholesterol oxidase procedure of Roelschlau et. al., Zeit. Klin. Chem. Lkin. Biochem., 12, 226 (1974). Triglycerides were determined by the combined method of lipase catalyzed hydrolysis of triglycerides to glycerol and free fatty acids [Bucolo, G. and David, H., Clin. Chem. 19, 476 (1973)] and Wahlefeld, A. W., in "Methods of Enzymatic Analysis", Vol. 4, Bergmeyer, H. U., Editor, Academic Press, New York, N.Y. (1974), pp. 1831-1835 and the enzymatic oxidation of the glycerol which leads to the production of colored formazan [Stavropoulos, W. S. and Crouch, R. D., Clin. Chem., 20, No. 7, 857 (1974)]. Changes in serum lipids are expressed as percent lowering from the values in control animals which did not receive drug treatment. Compounds which produce statistically significant lowering of either sterol or triglycerides are considered to be active. The results of this test on representative compounds appear in Table II.

TABLE II

| Compound | % Lowering of Serum Sterol | % Lowering of Serum Triglycerides |
|---|---|---|
| Ethyl 4-[11-(trimethylsilyl)undecylamino]benzoate | 43 | 22 |
| 4-[11-Trimethylsilyl)undecylamino]benzoic acid | 56 | 75 |
| Sodium 4-[11-(trimethylsilyl)undecylamino]benzoate | 52 | 54 |
| Ethyl 4-[14-(trimethylsilyl)tetradecylamino]benzoate | 47 | 38 |
| 4-[14-(Trimethylsilyl)tetradecylamino]benzoic acid | 60 | 70 |
| Sodium 4-[14-(trimethylsilyl)tetradecylamino]benzoate | 61 | 78 |
| Ethyl 4-[3-(trimethylsilyl)propylamino]benzoate | 23 | 46 |
| 4-[3-(Trimethylsilyl)propylamino]benzoic acid | 18 | 53 |
| Sodium 4-[3-(trimethylsilyl)propylamino]benzoate | 36 | 23 |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5 and 60% by weight.

The antiatherosclerotic effective dosage of active ingredient employed may vary depending on the particular compound employed, the mode of administration and the severity of the condition being treated. However, in general, satisfactory results are obtained when the compounds of the invention are administered at a daily dosage of from about 2 mg. to about 500 mg./kg. of animal body weight, preferably given in divided doses two to four times a day, or in sustained release form. For most large mammals, the total daily dosage is from about 100 mg. to about 5,000 mg. preferably from about 100 mg. to 2,000 mg. dosage forms suitable for internal use comprise from about 25 to 500 mg. of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. A decided practical advantage is that these active compounds may be administered orally as well as by intravenous, intramuscular, or subcutaneous routes if necessary. Solid carriers include starch, galactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, e.g., vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

EXAMPLE 1

14-(Trimethylsilyl)tetradecanol

The Grignard reagent prepared from 31.6 g. 3-(trimethylsilyl)propyl bromide and 4.0 g. magnesium turnings in 100 ml. dry tetrahydrofuran was dropwise added under argon to a cold (−20°) stirred solution of 33 g. 11-bromoundecyltetrahydropyranyl ether, 82 mg. lithium chloride and 125 mg. cuprus chloride in 250 mg. dry tetrahydrofuran. After the reagents had been combined, the solution was left to stir at room temperature for 17 hr. The reaction was diluted with 400 ml. 10% hydrochloric acid solution, the layers were separated, and the aqueous layer was extracted three times with 150 ml. portions of ether. The combined organic solutions were washed with brine, dried with anhydrous magnesium sulfate, and evaporated to 36.7 g. milky liquid. This intermediate tetrahydropyranyl ether was dissolved into 250 ml. ethanol and 15 ml. concentrated hydrochloric acid and stirred at reflux for 40 hr. The solvents were evaporated, the residue was re-dissolved into 300 ml. methylene chloride, and this solution was passed through a pad of hydrous magnesium silicate. The methylene chloride was evaporated and the residue was distilled in vacuo to yield a colorless liquid.

EXAMPLE 2

11-(Trimethylsilyl)undecyl bromide

The 3-(trimethylsilyl)propyl magnesium bromide prepared from 40 g. 3-(trimethylsilyl)propyl bromide and 5.1 g. magnesium turnings in 150 ml. dry ether was dropwise added to a cole (−20°) solution of 42 g. 1,8-dibromooctane, 170 mg. lithium chloride, and 270 mg. cuprus chloride in 120 ml. dry tetrahydrofuran under an argon atmosphere. When addition of the Grignard reagent was complete, the reaction was warmed to room temperature and stirring was continued for 17 hr. The solution was treated with 200 ml. 10% hydrochloric acid, the layers were separated, and the aqueous phase was washed twice with 100 ml. portions of ether. The combined organic phases were washed with brine, dried with anhydrous magnesium sulfate, and evaporated to a colorless liquid. Distillation of the crude product yielded the title compound.

EXAMPLE 3

14-(Trimethylsilyl)tetradecanoic acid

A solution of 240 g. 11-bromoundecanoic acid in 1.15 l. dry tetrahydrofuran was cooled to −20° under nitrogen, and to this stirred solution was dropwise added 309 ml. of a 3M solution of methyl magnesium bromide in ether followed by a solution of 1.54 g. lithium chloride and 2.43 g. cuprus chloride in 90 ml. dry tetrahydrofuran. The mixture was stirred at −20° while a warm solution of 3-(trimethylsilyl)propyl magnesium bromide, prepared from 266 g. 3-(trimethylsilyl)propyl bromide and 33.7 g. magnesium turnings in 860 ml. dry tetrahydrofuran, was added dropwise. The reaction was stirred at −20° for 30 min. after addition was complete, then at room temperature for 18 hr. The mixture was poured into 4 l. toluene and washed twice with 4 l. of 10% sulfuric acid and once with 4 l. 1N hydrochloric acid containing 375 ml. methanol. Evaporation of the toluene and distillation at reduced pressure yielded the title compound.

EXAMPLE 4

14-(trimethylsilyl)tetradecyloxy methanesulfonate

To a cold (−20°) stirred solution of 16.3 g. 14-(trimethylsilyl)tetradecanol and 9 ml. triethylamine in 150 ml. methylene chloride was dropwise added 4.9 ml. methanesulfonyl chloride at a rate such that the reaction temperature did not exceed −10°. The solution was warmed to room temperature, stirred for one hour, then extracted in sequence with 50 ml. each of ice-cold water, 10% hydrochloric acid, saturated sodium bicarbonate solution, and brine. The organic solution was dried with magenesium sulfate and evaporated to a light yellow, crystalline solid.

EXAMPLE 5

Ethyl 4-[14-(trimethylsilyltetradecanamido]benzoate

A solution of 225 g. 14-(trimethylsilyl)tetradecanoic acid in 300 ml. thionyl chloride was stirred for 4 hr. at room temperature, then this was evaporated to give 231 g. 14-(trimethylsilyl)tetradecanoyl chloride as an oil. The acid chloride was dissolved into 1.1 l. methylene chloride, and to this was added a solution of 123 g. ethyl 4-aminobenzoic acid and 149 ml. triethylamine in 1.1 l. methylene chloride at a rate such that reflux did not become excessive. The solution was refluxed for one hour, then stored at room temperature for 18 hr. The solvents were evaporated, the residue was taken up into 6 l. acetone, filtered, and the acetone was evaporated to yield the crude product. Crystallization from 1.5 l. chloroform followed by washing with cold acetonitrile afforded the title compound, m.p. 70°–72° C.

EXAMPLE 6

Ethyl 4-[3-(trimethylsilyl)propylamino]benzoate

A solution of 20 g. 3-(trimethylsilyl)propyl bromide and 33.9 g. ethyl 4-aminobenzoate in 75 ml. hexamethylphosphoramide was stirred at 100° for 18 hr. The cooled reaction was diluted with 100 ml. water, the layers were separated, and the aqueous layer was washed three times 100 ml. portions of methylene chloride. The combined organic solutions were washed with water and brine, dried with anhydrous magnesium sulfate, passed through a pad of hydrous magnesium silicate, and evaporated to 96 g. orange liquid. The liquid was dissolved into 100 ml. ethanol and the product was precipitated with 100 ml. water. The solid was filtered and dried. Crystallization from water-ethanol yielded the title compound as a white solid, m.p. 64°–66° C.

EXAMPLE 7

Ethyl 4-[14-(trimethylsilyl)tetradecylamino]benzoate

A 125 g. sample of ethyl 4-[14-(trimethylsilyl)tetradecanamido]benzoate was dissolved into 1 l. dry tetrahydrofuran, and to this stirred solution under nitrogen was dropwise added 419 ml. 1M borane in tetrahydrofuran. The solution was refluxed for four hours, cooled, and poured with stirring into 11.2 l. ice-water which contained about 250 g. sodium chloride. The precipitate was filtered off and air dried. Crystallization from ethanol afforded the pure product, m.p. 91°–92° C.

EXAMPLE 8

Ethyl 4-[14-(trimethylsilyl)tetradecylamino]benzoate

A solution of 20.8 g. 14-(trimethylsilyl)tetradecyloxy methanesulfonate and 20 g. ethyl 4-aminobenzoate in 50 ml. hexamethylphosphoramide was stirred at 110° for 18 hr. The reaction was diluted with 100 ml. water and extracted three times with 150 ml. portions of methylene chloride. The combined organic layers were washed with brine, dried with anhydrous magnesium sulfate, passed through a pad of hydrous magnesium silicate, and evaporated. The residue was crystallized from 250 ml. ethanol to yield the title compound as a crystalline solid, m.p. 91°–92° C.

EXAMPLE 9

4-[14-(Trimethylsilyl)tetradecylamino]benzoic acid

A solution of 14.1 g. ethyl 4-[14-(trimethylsilyl)tetradecylamino]benzoate and 6.4 g. 85% potassium hydroxide in 150 ml. 95% ethanol was heated at 75° for 5 hr. The reaction was diluted with 300 ml. water and adjusted to pH 3.5 with concentrated hydrochloric acid. The precipitate was filtered, dried, and crystallized from acetone to yield a white solid, m.p. 105°–107° C.

EXAMPLE 10

Sodium 4-[14-(trimethylsilyl)tetradecylamino]benzoate

To a stirred, hot solution of 4.5 g. 4-[14-(trimethylsilyl)tetradecylamino]benzoic acid in 150 ml. absolute ethanol was added 2.2 ml. 10N sodium hydroxide. The solution was cooled and the precipitate was filtered off and dried to yield a light yellow solid, m.p. 350°–355° C. dec.

EXAMPLE 11

Ethyl 4-[11-(trimethylsilyl)undecylamino]benzoate

In the manner of example 3, 11-(trimethylsilyl)undecyl bromide was reacted with ethyl 4-aminobenzoate to yield ethyl 4-[11-(trimethylsilyl)undecylamino]benzoate, m.p. 66°–68° C.

TABLE III

The following benzoate esters are prepared from reaction of ethyl 4-aminobenzoate with the appropriate halide or methanesulfonate as described in Examples 6 or 8, or from appropriate acyl chlorides followed by diborane reduction as described in Example 5 and 7. Trialkylsilylalkyl halides, methanesulfonates, or trialkylsilylalkanoic acids required for these reactions are prepared by the methods of Examples 1–4.

| Examples No. | Compound |
|---|---|
| 12 | Ethyl 4-[4-(trimethylsilyl)butylamino]benzoate |
| 13 | Ethyl 4-[5-(trimethylsilyl)pentylamino]benzoate |
| 14 | Ethyl 4-[6-(trimethylsilyl)hexylamino]benzoate |
| 15 | Ethyl 4-[7-(trimethylsilyl)heptylamino]benzoate |
| 16 | Ethyl 4-[8-(trimethylsilyl)octylamino]benzoate |
| 17 | Ethyl 4-[9-(trimethylsilyl)nonylamino]benzoate |
| 18 | Ethyl 4-[10-(trimethylsilyl)decylamino]benzoate |
| 19 | Ethyl 4-[12-(trimethylsilyl)dodecylamino]benzoate |
| 20 | Ethyl 4-[13-(trimethylsilyl)tridecylamino]benzoate |
| 21 | Ethyl 4-[15-(trimethylsilyl)pentadecylamino]benzoate |
| 22 | Ethyl 4-[16-(trimethylsilyl)hexadecylamino]benzoate |
| 23 | Ethyl 4-[17-(trimethylsilyl)heptadecylamino]benzoate |
| 24 | Ethyl 4-[18-(trimethylsilyl)octadecylamino]benzoate |
| 25 | Ethyl 4-[19-(trimethylsilyl)nonadecylamino]benzoate |
| 26 | Ethyl 4-[20-(trimethylsilyl)eicosylamino]benzoate |
| 27 | Ethyl 4-[3-(hexyldimethylsilyl)propylamino]benzoate |
| 28 | Ethyl 4-[11-(hexyldimethylsilyl)undecylamino]benzoate |
| 29 | Ethyl 4-[14-(hexyldimethylsilyl)tetradecylamino]benzoate |
| 30 | Ethyl 4-[3-(cyclohexyldimethylsilyl)propylamino]benzoate |
| 31 | Ethyl 4-[14-(cyclohexyldimethylsilyl)tetradecylamino]benzoate |
| 32 | Ethyl 4-[3-(t-butyldimethylsilyl)propylamino]benzoate |
| 33 | Ethyl 4-[11-(t-butyldimethylsilyl)undecylamino]benzoate |
| 34 | Ethyl 4-[14-(t-butyldimethylsilyl)tetradecylamino]benzoate |
| 35 | Ethyl 4-[3-(trihexylsilyl)propylamino]benzoate |
| 36 | Ethyl 4-[11-(trihexylsilyl)undecylamino]benzoate |
| 37 | Ethyl 4-[14-(trihexylsilyl)tetradecylamino]benzoate |
| 38 | Ethyl 4-[19-(trihexylsilyl)nonadecylamino]benzoate |
| 39 | Ethyl 4-[3-(triethylsilyl)propylamino]benzoate |

TABLE III-continued

The following benzoate esters are prepared from reaction of ethyl 4-aminobenzoate with the appropriate halide or methanesulfonate as described in Examples 6 or 8, or from appropriate acyl chlorides followed by diborane reduction as described in Example 5 and 7. Trialkylsilylalkyl halides, methanesulfonates, or trialkylsilylalkanoic acids required for these reactions are prepared by the methods of Examples 1–4.

| Examples No. | Compound |
|---|---|
| 40 | Ethyl 4-[11-(triethylsilyl)undecylamino]benzoate |
| 41 | Ethyl 4-[14-(triethylsilyl)tetradecylamino]benzoate |
| 42 | Ethyl 4-[3-(tripropylsilyl)propylamino]benzoate |
| 43 | Ethyl 4-[11-(tripropylsilyl)undecylamino]benzoate |
| 44 | Ethyl 4-[14-(tripropylsilyl)tetradecylamino]benzoate |
| 45 | Ethyl 4-[3-(pentyldimethylsilyl)propylamino]benzoate |
| 46 | Ethyl 4-[11-(pentyldimethylsilyl)undecylamino]benzoate |
| 47 | Ethyl 4-[14-(pentyldimethylsilyl)tetradecylamino]benzoate |
| 48 | Ethyl 4-[3-(ethylhexylmethylsilyl)propylamino]benzoate |
| 49 | Ethyl 4-[11-(ethylhexylmethylsilyl)undecylamino]benzoate |
| 50 | Ethyl 4-[14-(ethylhexylmethylsilyl)tetradecylamino]benzoate |
| 51 | Ethyl 4-[3-[2-(3-cyclohexenyl)ethyldimethylsilyl]propylamino]benzoate |
| 52 | Ethyl 4-[11-[2-(3-cyclohexenyl)ethyldimethylsilyl]undecylamino]benzoate |
| 53 | Ethyl 4-[14-[2-(3-cyclohexenyl)ethyldimethylsilyl]tetradecylamino]benzoate |

EXAMPLE 54

4-[3-(Trimethylsilyl)propylamino]benzoic acid

A sample of 15 g. ethyl 4-[3-(trimethylsilyl)propylamino]benzoate was converted by the method of Example 9 to the title compound as a white, crystalline product, m.p. 164°–165° C.

EXAMPLE 55

4-[11-(Trimethylsilyl)undecylamino]benzoic acid

A sample of 16 g. ethyl 4-[11-(trimethylsilyl)undecylamino]benzoate was converted to the title compound, m.p. 121°–122° C. by the method of Example 9 to yield white needles.

TABLE IV

The following benzoic acids are prepared from the corresponding carboxylate esters of TABLE III by the method of Example 9.

| Example No. | Compound |
|---|---|
| 56 | 4-[4-(Trimethylsilyl)butylamino]benzoic acid |
| 57 | 4-[5-(Trimethylsilyl)pentylamino]benzoic acid |
| 58 | 4-[6-(Trimethylsilyl)hexylamino]benzoic acid |
| 59 | 4-[7-(Trimethylsilyl)heptylamino]benzoic acid |
| 60 | 4-[8-(Trimethylsilyl)octylamino]benzoic acid |
| 61 | 4-[9-(Trimethylsilyl)nonylamino]benzoic acid |
| 62 | 4-[10-(Trimethylsilyl)decylamino]benzoic acid |
| 63 | 4-[12-(Trimethylsilyl)dodecylamino]benzoic acid |
| 64 | 4-[13-(Trimethylsilyl)tridecylamino]benzoic acid |
| 65 | 4-[15-(Trimethylsilyl)pentadecylamino]benzoic acid |
| 66 | 4-[16-(Trimethylsilyl)hexadecylamino]benzoic acid |
| 67 | 4-[17-(Trimethylsilyl)heptadecylamino]benzoic acid |
| 68 | 4-[18-(Trimethylsilyl)octadecylamino]benzoic acid |
| 69 | 4-[19-(Trimethylsilyl)nonadecylamino]benzoic acid |
| 70 | 4-[20-(Trimethylsilyl)eicosylamino]benzoic acid |
| 71 | 4-[3-(Hexyldimethylsilyl)propylamino]benzoic acid |
| 72 | 4-[11-(Hexyldimethylsilyl)undecylamino]benzoic acid |
| 73 | 4-[14-(Hexyldimethylsilyl)tetradecylamino]benzoic acid |
| 74 | 4-[3-(Cyclohexyldimethylsilyl)propylamino]benzoic acid |
| 75 | 4-[14-(Cyclohexyldimethylsilyl)tetradecylamino]benzoic acid |
| 76 | 4-[3-(5-Butyldimethylsilyl)propylamino]benzoic acid |
| 77 | 4-[11-(t-Butyldimethylsilyl)undecylamino]benzoic acid |
| 78 | 4-[14-(t-Butyldimethylsilyl)tetradecylamino]benzoic acid |
| 79 | 4-[3-(Trihexylsilyl)propylamino]benzoic acid |
| 80 | 4-[11-(Trihexylsilyl)undecylamino]benzoic acid |
| 81 | 4-[14-(Trihexylsilyl)tetradecylamino]benzoic acid |
| 82 | 4-[19-(Trihexylsilyl)nonadecylamino]benzoic acid |
| 83 | 4-[3-(Triethylsilyl)propylamino]benzoic acid |
| 84 | 4-[11-(Triethylsilyl)undecylamino]benzoic acid |
| 85 | 4-[14-(Triethylsilyl)tetradecylamino]benzoic acid |
| 86 | 4-[3-(Tripropylsilyl)propylamino]benzoic acid |
| 87 | 4-[11-(Tripropylsilyl)undecylamino]benzoic acid |
| 88 | 4-[14-(Tripropylsilyl)tetradecylamino]benzoic acid |
| 89 | 4-[3-(Pentyldimethylsilyl)propylamino]benzoic acid |
| 90 | 4-[11-(Pentyldimethylsilyl)undecylamino]benzoic acid |
| 91 | 4-[14-(Pentyldimethylsilyl)tetradecylamino]benzoic acid |
| 92 | 4-[3-(Ethylhexylmethylsilyl)propylamino]benzoic acid |
| 93 | 4-[11-(Ethylhexylmethylsilyl)undecylamino]benzoic acid |
| 94 | 4-[14-(Ethylhexylmethylsilyl)tetradecylamino]benzoic acid |
| 95 | 4-[3-[2-(3-Cyclohexenyl)ethyldimethylsilyl]propylamino]benzoic acid |
| 96 | 4-[11-[2-(3-Cyclohexenyl)ethyldimethylsilyl]undecylamino]benzoic acid |
| 97 | 4-[14-[2-(3-cyclohexenyl)ethyldimethylsilyl]tetradecylamino]benzoic acid |

EXAMPLE 98

Sodium 4-[3-(trimethylsilyl)propylamino]benzoate

4-[3-(Trimethylsilyl)propylamino]benzoic acid was converted to the title compound, m.p. 385°–388° C. dec., by the method of Example 10.

EXAMPLE 99

Sodium 4-[11-(trimethylsilyl)undecylamino]benzoate

4-[11-(Trimethylsilyl)undecylamino]benzoic acid of Example 55 was converted to the title compound, m.p. 350°–370° C. dec., by the method of Example 10.

TABLE V

The following sodium salts of benzoic acids are prepared from the corresponding acids of Table IV by the method of Example 10.

| Example No. | Compound |
|---|---|
| 100 | Sodium 4-[4-(trimethylsilyl)butylamino]benzoate |
| 101 | Sodium 4-[5-(trimethylsilyl)pentylamino]benzoate |
| 102 | Sodium 4-[6-(trimethylsilyl)hexylamino]benzoate |
| 103 | Sodium 4-[7-(trimethylsilyl)heptylamino]benzoate |
| 104 | Sodium 4-[8-(trimethylsilyl)octylamino]benzoate |
| 105 | Sodium 4-[9-(trimethylsilyl)nonylamino]benzoate |
| 106 | Sodium 4-[10-(trimethylsilyl)decylamino]benzoate |
| 107 | Sodium 4-[12-(trimethylsilyl)dodecylamino]benzoate |
| 108 | Sodium 4-[13-(trimethylsilyl)tridecylamino]benzoate |
| 109 | Sodium 4-[15-(trimethylsilyl)pentadecylamino]benzoate |
| 110 | Sodium 4-[16-(trimethylsilyl)hexadecylamino]benzoate |
| 111 | Sodium 4-[17-(trimethylsilyl)heptadecylamino]benzoate |
| 112 | Sodium 4-[18-(trimethylsilyl)octadecylamino]benzoate |
| 113 | Sodium 4-[19-(trimethylsilyl)nonadecylamino]benzoate |
| 114 | Sodium 4-[20-(trimethylsilyl)eicosylamino]benzoate |
| 115 | Sodium 4-[3-(hexyldimethylsilyl)propylamino]benzoate |
| 116 | Sodium 4-[11-(hexyldimethylsilyl)undecylamino]benzoate |
| 117 | Sodium 4-[14-(hexyldimethylsilyl)tetradecylamino]benzoate |
| 118 | Sodium 4-[3-(cyclohexyldimethylsilyl)propylamino]benzoate |
| 119 | Sodium 4-[14-(cyclohexyldimethylsilyl)tetradecylamino]benzoate |
| 120 | Sodium 4-[3-(t-butyldimethylsilyl)propylamino]benzoate |
| 121 | Sodium 4-[11-(t-butyldimethylsilyl)undecylamino]benzoate |
| 122 | Sodium 4-[14-(t-butyldimethylsilyl)tetradecylamino]benzoate |
| 123 | Sodium 4-[3-(trihexylsilyl)propylamino]benzoate |
| 124 | Sodium 4-[11-(trihexylsilyl)undecylamino]benzoate |
| 125 | Sodium 4-[14-(trihexylsilyl)tetradecylamino]benzoate |
| 126 | Sodium 4-[19-(trihexylsilyl)nonadecylamino]benzoate |
| 127 | Sodium 4-[3-(triethylsilyl)propylamino]benzoate |
| 128 | Sodium 4-[11-(triethylsilyl)undecylamino]benzoate |
| 129 | Sodium 4-[14-(triethylsilyl)tetradecylamino]benzoate |
| 130 | Sodium 4-[3-(tripropylsilyl)propylamino]benzoate |
| 131 | Sodium 4-[11-(tripropylsilyl)undecylamino]benzoate |
| 132 | Sodium 4-[11-(tripropylsilyl)tetradecylamino]benzoate |
| 133 | Sodium 4-[3-(pentyldimethylsilyl)propylamino]benzoate |

TABLE V-continued

The following sodium salts of benzoic acids are prepared from the corresponding acids of Table IV by the method of Example 10.

| Example No. | Compound |
|---|---|
| 134 | Sodium 4-[11-(pentyldimethylsilyl)undecylamino]benzoate |
| 135 | Sodium 4-[14-(pentyldimethylsilyl)tetradecylamino]benzoate |
| 136 | Sodium 4-[3-(ethylhexylmethylsilyl)propylamino]benzoate |
| 137 | Sodium 4-[11-(ethylhexylmethylsilyl)undecylamino]benzoate |
| 138 | Sodium 4-[14-(ethylhexylmethylsilyl)tetradecylamino]benzoate |
| 139 | Sodium 4-[3-[2-(3-cyclohexenyl)ethyldimethylsilyl]propylamino]benzoate |
| 140 | Sodium 4-[11-[2-(3-cyclohexenyl)ethyldimethylsilyl]undecylamino]benzoate |
| 141 | Sodium 4-[14-[2-(3-cyclohexenyl)ethyldimethylsilyl]tetradecylamino]benzoate |

EXAMPLE 142

4-[14-(Trimethylsilyl)tetradecylamino]benzoyl chloride hydrochloride

Into a cold solution of 15 g. 4-[14-(trimethylsilyl)tetradecylamino]benzoic acid in dimethoxyethanemethylene chloride (4:1) is bubbled dry hydrogen chloride gas until no more precipitate forms. The solution is treated with 25 ml. thionyl chloride and refluxed until all of the precipitate is redissolved. The solution is evaporated to yield the title compound.

EXAMPLE 143

4-[N-Trifluoroacetyl-14-(trimethylsilyl)tetradecylamino]benzoyl chloride

A stirred ice-cold suspension of 9 g. 4-[14-(trimethylsilyl)tetradecylamino]benzoic acid in 100 ml. of dimethoxyethane and 16 ml. of pyridine is treated with 18 ml. of trifluoroacetic anhydride at 0° C. The solution is stirred at 0° C. for 30 minutes then at room temperature and then diluted with 300 ml. ether and 100 g. ice. After stirring vigorously for 15 minutes, the phases are separated, the ether solution is washed with brine, dried and evaporated to a white, amorphous solid.

To a solution of 9.2 g. of the above solid in 30 ml. methylene chloride and 0.5 ml. dimethylformamide is added 5.7 ml. thionyl chloride. After 20 hours at reflux, the solvents are evaporated to yield 4-[N-trifluoroacetyl-14-(trimethylsilyl)tetradecylamino]benzoyl chloride as a light yellow, mobile oil.

EXAMPLE 144

4-[N-Carbobenzyloxy-14-(trimethylsilyl)tetradecylamino]benzoyl chloride

To 15 g. 4-[14-(trimethylsilyl)tetradecylamino]benzoic acid in 200 ml. warm chloroform is added a solution of 15 g. of sodium carbonate in 150 ml. water. To the vigorously stirred solution is added 10 g. carbobenzyloxy chloride. After 2 hours stirring at 40° C., the layers are separated, washed three times with 1N hydrochloric acid, dried, and evaporated to an oil. The oil is dissolved in 300 ml. toluene, treated with 15 ml. thionyl chloride and the solution is refluxed for 5 hours. The solvents are evaporated and the residue is dissolved three times in toluene, and evaporated to a viscous, orange oil.

EXAMPLE 145

1-[4-[N-tery-Butyloxycarbonyl-14-(trimethylsilyl)tetradecylamino]benzoyl)imidazole A solution of 10 g. 4-[14-(trimethylsilyl)tetradecylamino]benzoic acid in 100 ml. dioxane is treated with 4.0 g. tert-butylazidoformate and 10 ml. pyridine. After stirring at room temperature for 18 hours, the protected amido-acid is precipitated from solution by the addition of 150 ml. water. The solid is collected, thoroughly dried, and dissolved in 200 ml. of a mixture consisting of methylene chloride/dimethoxyethane/pyridine (1:4:1). To this solution is added 5.4 g. 1,1'-carbonyldiimidazole. The solution is stirred overnight at room temperature and the solvents are evaporated to yield 1-[4-[N-tert-butyloxycarbonyl-14-(trimethylsilyl)-tetradecylamino]benzoyl]imidazole as an orange oil.

EXAMPLE 146

2,3-Dihydroxypropyl 4-[14-(trimethylsilyl)tetradecylamino]benzoate

A solution of 7.17 g. of 4-[14-(trimethylsilyl)tetradecylamino]benzoic acid, 4.80 g. of 25% aqueous sodium hydroxide, and 12.6 g. of 3-iodo-1,2-propanediol in 50 ml. of hexamethylphosphoramide is stirred for 24 hours at ambient temperature, diluted with 100 ml. of ether and stirred for 5 days at ambient temperature. The mixture is treated with water and extracted with ether. The dried extracts are evaporated to yield the product as a white solid.

EXAMPLE 147

Methyl 4-[14-(trimethylsilyl)tetradecylamino]benzoate

A solution of 7.0 g. of 4-[14-(trimethylsilyl)tetradecylamino)benzoic acid in 25 ml. of hexamethylphosphoramide is added to a stirred mixture of 0.800 g. of sodium hydride (57% in mineral oil) and 25 ml. of hexamethylphosphoramide. The solution which forms after one hour is treated with 11.0 g. of methyl iodide and is then stirred at 25° C. for 18 hours. Dilution with water followed by filtration affords a white solid which is crystallized from ethanol to yield the product as a white solid.

EXAMPLE 148

3-Hydroxypropyl 4-[14-(trimethylsilyl)tetradecylamino]benzoate

A mixture of 2.2 g. of methyl 4-[14-(trimethylsilyl)tetradecylamino]benzoate, 280 mg. of 1,3-propanediol and 1.37 g. of p-toluenesulfonic acid is heated at 180° C. for 18 hours and then is partitioned between ether and 3% aqueous sodium carbonate solution. The ether layer is separated, dried, and evaporated to yield the product as a white solid.

EXAMPLE 149

2-Ethoxyethyl 4-[14-(trimethylsilyl)tetradecylamino]benzoate

A solution of 11.5 g. of 4-[14-(trimethylsilyl)tetradecylamino]benzoic acid, 1.00 g. of 2-ethoxyethanol and 5.35 ml. of boron trifluoride etherate in 200 ml. of toluene is stirred at reflux for 48 hours. The solution is treated with an additional 5.35 ml. of boron trifluoride etherate and refluxing is continued for 120 hours. Dilution with water and methylene chloride followed by filtration affords the product as a white solid.

EXAMPLE 150

Isopropyl 4-[14-(trimethylsilyl)tetradecylamino]benzoate

A solution of 4.9 g of 4-[14-(trimethylsilyl)tetradecylamino]benzoic acid and 3.4 ml. of boron trifluoride etherate in 20 ml. of isopropyl alcohol is stirred at reflux for 44 hours, allowed to cool, and poured into 120 ml. of ice cold 5% aqueous sodium carbonate solution. The white solid is colleectd by filtration and recrystallized from benzene-ethanol to yield the product as a white solid.

EXAMPLE 151

1-(Methoxycarbonyl)propyl 4-[14-(trimethylsilyl)tetradecylamino]benzoate

To a solution of 10.0 g. 4-[14-(trimethylsilyl)tetradecylamino]benzoyl chloride hydrochloride in 200 ml. methylene chloride is added dropwise a solution of 3 g. methyl α-hydroxybutyrate and 5 g. triethylamine in 100 ml. ether. After 17 hours stirring at room temperature, the precipitate is collected and washed with several portions of ether. The ether solution is washed with water, dried and evaporated to yield the product as a white solid.

EXAMPLE 152

1-Carboxyethyl 4-[14-(trimethylsilyl)tetradecylamino]benzoate

A flask containing 10.0 g. 4-[14-(trimethylsilyl)tetradecylamino]benzoic acid, 3.4 g. lactic acid, 500 mg. toluenesulfonic acid and 500 ml. toluene is equipped with a Soxhlet extractor charged with activated 4A Linde molecular sieves. The solution is refluxed for 24 hours, during which time the Soxhlet extractor is charged twice more with fresh sieves. The hot solution is filtered and allowed to cool, whereupon the product separates as off-white crystals.

EXAMPLE 153

Diethyl 0-[4-[15-(trimethylsilyl)tetradecylamino]benzoyl]tartrate

A mixture of 6.3 g. 4-[N-trifluoroacetyl)-14-(trimethylsilyl)tetradecylamino)benzoyl chloride and 1.2 g. triethylamine in 100 ml. warm ether is treated with 2.5 g. diethyl tartarate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the product as a white, crystalline solid.

EXAMPLE 154

0-[4-[14-(Trimethylsilyl)tetradecylamino]benzoyl]malic acid

A warm solution of 8.0 g. 4-[N-carbobenzyloxy-N-(trimethylsilyl)tetradecylamino]benzoyl chloride and 1.3 g. triethylamine in 100 ml. ether is treated with 2 g. malic acid. The mixture is refluxed for one hour and filtered while hot. The solid precipitate is washed several times with hot ether, then the ether is evaporated to yield a white solid. The product is dissolved in tetrahydrofuran (100 ml.) and hydrogenated over 600 mg. 10% palladium-on-carbon at 50 psi until hydrogen uptake stops. The catalyst is filtered, and the solution is evaporated to yield the product as a white solid.

EXAMPLE 155

2-(Ethoxycarbonyl)vinyl 4-[14-(trimethylsilyl)tetradecylamino]benzoate

To a mixture containing 4.2 g. 1-[4-[N-tert-butyloxycarbonyl-14-(trimethylsilyl)tetradecylamino]benzoyl]imidazole in 50 ml. 5N sodium hydroxide is added 3 g. ethyl α-formyl acetate. The solution is vigorously stirred for 24 hours. The layers are separated, and the chloroform solution is washed once with 50 ml. 1N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of the product.

TABLE VI

The following esters are prepared from the acids of Table IV (or activated derivatives thereof prepared by the methods of Examples 142-145) by the methods of Examples 146-155 as shown in the table.

| Example No. | Method of Example | Compound |
|---|---|---|
| 156 | 146 | 2,3-Dihydroxypropyl 4-[11-(trimethylsilyl)undecylamino]benzoate |
| 157 | 146 | 2,3-Dihydroxypropyl 4-[3-(hexyldimethylsilyl)propylamino]benzoate |
| 158 | 146 | 2,3-Dihydroxypropyl 4-[14-(t-butyldimethylsilyl)tetradecylamino]benzoate |
| 159 | 146 | 2,3-Dihydroxypropyl 4-[11-(ethylhexylmethylsilyl)undecylamino]benzoate |
| 160 | 147 | Methyl 4-[17-(trimethylsilyl)heptadecylamino]benzoate |
| 161 | 147 | Methyl 4-[14-(cyclohexyldimethylsilyl)tetradecylamino]benzoate |
| 162 | 147 | Methyl 4-[3-(tripropylsilyl)propylamino]benzoate |
| 163 | 147 | Methyl 4-[11-(pentyldimethyl)undecylamino]benzoate |
| 164 | 147 | Methyl 4-[3-[2-(3-cyclohexenyl)-ethyldimethylsilyl]propylamino]benzoate |
| 165 | 148 | 2-Hydroxypropyl 4-[14-(trimethylsilyl)tetradecylamino]benzoate |
| 166 | 148 | 3-Hydroxypropyl 4-[11-(t-butyldimethylsilyl)undecylamino]benzoate |
| 167 | 148 | 3-Hydroxypropyl 4-[14-(pentyldimethylsilyl)tetradecylamino]benzoate |
| 168 | 148 | 4-Hydroxybutyl 4-[16-(trimethylsilyl)hexadecylamino]benzoate |
| 169 | 149 | 2-Ethoxyethyl 4-[11-(t-butyldimethylsilyl)undecylamino]benzoate |
| 170 | 149 | 2-Ethoxyethyl 4-[3-(triethylsilyl)propylamino]benzoate |
| 171 | 150 | Isopropyl 4-[11-(trimethylsilyl)undecylamino]benzoate |
| 172 | 150 | Isopropyl 4-[14-(ethylhexylmethylsilyl)tetradecylamino]benzoate |
| 173 | 150 | Isopropyl 4-[11-(t-butyldimethylsilyl)undecylamino]benzoate |
| 174 | 151 | 1-(Methoxycarbonyl)propyla 4-[14-trimethylsilyltetradecylamino]benzoate |
| 175 | 152 | 1-Carboxyethyl 4-[11-(trimethylsilyl)undecylamino]benzoate |
| 176 | 152 | 1-Carboxyethyl 4-[14-(pentyldemethylsilyl)tetradecylamino]benzoate |
| 177 | 153 | Diethyl 0-[4-[14-(trimethylsilyl)tetradecylamino]benzoyl]tartrate |
| 178 | 154 | 0-[4-[3-(cyclohexyldimethylsilyl)propylamino]benzoyl]malic acid |
| 179 | 154 | 0-[4-[11-(pentyldimethylsilyl)undecylamino]benzoyl]malic acid |

TABLE VI-continued

The following esters are prepared from the acids of Table IV (or activated derivatives thereof prepared by the methods of Examples 142-145) by the methods of Examples 146-155 as shown in the table.

| Example No. | Method of Example | Compound |
|---|---|---|
| 180 | 155 | 2-(Ethoxycarbonyl)vinyl 4-[11-(trimethylsilyl)undecylamino]benzoate |
| 181 | 155 | 2-(Ethoxycarbonyl)vinyl 4-[14-(t-butyldimethylsilyl)tetradecylamino]benzoate |
| 182 | 155 | 2-(Ethoxycarbonyl)vinyl 4-[3-(ethylhexylmethylsilyl)propylamino]benzoate |

EXAMPLE 183

1-[4-[14-(Trimethylsilyl)tetradecylamino]benzoyl]-piperidine

To a chilled solution of 35 ml. of piperdine, 2.5 ml. of triethylamine and 0.6 g of 4-(dimethylamino)pyridine in 100 ml. of diethyl ether is added (½ hour) a solution of 8.1 g. of 4-[14-(trimethylsilyl)tetradecylamino)-benzoyl chloride hydrochloride in 50 ml. of ether. The solution is warmed to room temperature and maintained there for two hours. The solution is heated to reflux for an additional 2 hours at which time the reaction is complete. The solution is cooled, extracted twice with water and dried. The solvent is removed in vacuo and the solid is recrystallized to yield the product as a white solid.

EXAMPLE 184

Ethyl 4-[14-(trimethylsilyl)tetradecylamino]hippurate

A solution of 20 g. 4-[14-(trimethylsilyl)tetradecylamino]benzoyl chloride hydrochloride in 100 ml. dioxane is added to 4.9 g. freshly prepared ethyl glycinate in 300 ml. of methylene chloride containing 1 g. of 4-(dimethylamino)pyridine and 10 ml. of triethylamine. After 16 hours at room temperature the reaction is refluxed for 2 hours, cooled and filtered. The mother liquor is extracted with water and 10% hydrochloric acid. The solution is dried and concentrated in vacuo to an amber liquid. A sample is chromatographed on silica, appropriate fractions are pooled and evaporated to yield a solid which is recrystallized to a white solid.

EXAMPLE 185

N-[4-[14-(Trimethylsilyl)tetradecylamino]benzoyl)glycine

A mixture of 12.5 g. of ethyl 4-[14-(trimethylsilyl)tetradecylamino]hippurate, 55 ml. of 1N sodium hydroxide solutions and 50 ml. of ethanol is stirred at ambient temperature for 2 hours and then partially evaporated. The aqueous solution is washed with diethyl ether, acidified with 6N hydrochloric acid, and filtered. The solid is dried in vacuo and recrystallized to yield the product as a white solid.

EXAMPLE 186

4-[14-(Trimethylsilyl)tetradecylamino]-N-(phenylsulfonyl)benzamide

A solution of 30.7 g. of benzenesulfonamide in 250 ml. of dry dimethylacetamide is added dropwise, with stirring and cooling, to a suspension of 5.4 g. of sodium hydride in 100 ml. of dry dimethylacetamide during 30 minutes at room temperature. Stirring is continued for 30 minutes. In the meantime, a mixture of 36.2 g. of 4-[14-(trimethylsilyl)tetradecylamino] benzoic acid in 100 ml. of methylene chloride, 300 ml. of dimethoxyethane, and 40 ml. of thionyl chloride is refluxed for 1 hour and 15 minutes. The solution is evaporated and to the resulting oil residue is added, in one portion, the previously prepared mixture of sodium benzenesulfonamide in dimethylacetamide. The mixture is stirred for 30 minutes and then filtered. The filtrate is poured into 2 liters of water and 250 ml. of saturated sodium chloride solution. The product is collected by filtration and then dissolved in methylene chloride, the mixture is filtered through diatomaceous earth, and brine is added. The layers are separated, the organic phase is dried and evaporated. The residue is crystallized to yield the product as a white solid.

EXAMPLE 187

N-[4-[14-(Trimethylsilyl)tetradecylamino]benzoyl]methanesulfonamide

A solution of 12.3 g. of 4-[14-(trimethylsilyl)tetradecylamino]benzoyl chloride hydrochloride and 2.8 g. of methanesulfonamide in 150 ml. of pyridine is stirred at reflux for 2 hours and then evaporated in vacuo. The residue is partitioned between water and diethyl ether, the aqueous layer acidified with 1N hydrochloric acid, and the organic layer separated, dried with magnesium sulfate and evaporated. Crystallization of the residue affords the product as a white solid.

EXAMPLE 188

N-[4-[14-(Trimethylsilyl)tetradecylamino]benzoyl]alanine

A solution of 4.64 g. of 4-[N-trifluoroacetyl-14-(trimethylsilyl)tetradecylamino]benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization yields the product as a white, crystalline solid.

EXAMPLE 189

N-[4-[14-(Trimethylsilyl)tetradecylamino]benzoyl]benzamide

One gram of a 50% oil dispersion of sodium hydride is washed with petroleum ether by decantation, dried and suspended in 5 ml. of tetrahydrofuran. To this stirred mixture is added a solution of 2.42 g. of benzamide in 5 ml. of tetrahydrofuran in one portion. After stirring for 30 min., a solution of 0.9 g. of 4-[N-trifluoroacetyl-14(trimethylsilyl)tetradecylamino]benzoyl chloride in 3 ml. of tetrahydrofuran is added dropwise during 5 minutes to the mixture. The mixture is stirred at room temperature under nitrogen for one hour. The mixture is then poured into water and extracted with ether. The ether extract is washed with water and brine and dried with sodium sulfate. Evaporation and recrystallization yields the product as a white solid.

EXAMPLE 190

N-(2,3-Dihydroxypropyl)-4-[14-(trimethylsilyl)tetradecylamino]benzamide

To a mixture containing 4.2 g. of 1-[4-[N-(tert-butyloxycarbonyl)-4-[14-(trimethylsilyl)tetradecylamino]benzoyl)imidazole, 50 ml. of chloroform, and 50 ml. of 5N sodium hydroxide is added 1.1 g. of 3-amino-1,2-propanediol. The solution is vigorously stirred for 24 hours, the layers are separated, and the chloroform solution is washed once with 50 ml. of 1N sodium hydroxide. The solvent is evaporated and the residue is heated for 30 minutes at 40° C. in 50 ml. of anhydrous trifluoroacetic acid. The solvent is again evaporated and the oil is crystallized to yield the product as a light yellow solid.

TABLE VII

The following benzamides are prepared from the corresponding carboxylic acids of Table IV (or activated derivatives thereof prepared by the methods of Examples 142–145) by the methods of Examples 183–190 as shown in the table.

| Example No. | Method of Example | Compound |
| --- | --- | --- |
| 191 | 183 | 1-[4-[6-(Trimethylsilyl)hexylamino]benzoyl]piperidine |
| 192 | 183 | 1-[4-[11-(Hexyldimethylsilyl)undecylamino]benzoyl]piperidine |
| 193 | 183 | 1-[4-[14-(Ethylhexylmethylsilyl)-tetradecylamino]benzoyl]piperidine |
| 194 | 183 | 1-[4-[14-(Trimethylsilyl)tetradecylamino]benzoyl]pyrrolidine |
| 195 | 183 | 1-[4-[11-(t-Butyldimethylsilyl)undecylamino]benzoyl]pyrrolidine |
| 196 | 184 | Ethyl 4-[7-(trimethylsilyl)heptylamino]hippurate |
| 197 | 184 | Ethyl 4-[4-[14-(cyclohexyldimethylsilyl)tetradecylamino]hippurate |
| 198 | 184 | Ethyl 4-[3-(trihexylsilyl)propylamino]hippurate |
| 199 | 184 | Ethyl 4-[11-(t-butyldimethylsilyl)-undecylamino]hippurate |
| 200 | 185 | N—[4-[7-(Trimethylsilyl)heptylamino]-benzoyl]glycine |
| 201 | 185 | N—[4-[14-(Cyclohexyldimethylsilyl)-tetradecylamino]benzoyl]glycine |
| 202 | 185 | N—[4-[3-(Trihexylsilyl)propylamino]-benzoyl]glycine |
| 203 | 185 | N—[4-[11-(t-Butyldimethylsilyl)undecylamino]benzoyl]glycine |
| 204 | 186 | 4-[13-(Trimethylsilyl)tridecylamino]-N—(phenylsulfonyl)benzamide |
| 205 | 186 | 4-[11-(t-Butyldimethylsilyl)undecylamino]-N—(phenylsulfonyl)benzamide |
| 206 | 186 | 4-[3-(Triethylsilyl)propylamino]-N—(phenylsulfonyl)benzamide |
| 207 | 186 | 4-[11-(Pentyldimethylsilyl)undecylamino]-N—(phenylsulfonyl)benzamide |
| 208 | 187 | N—[4-[16-(Trimethylsilyl)hexadecylamino]benzoyl]methanesulfonamide |
| 209 | 187 | N—[4-[11-(Triethylsilyl)undecylamino]benzoyl]methanesulfonamide |
| 210 | 187 | N—[4-[3-(Pentyldimethylsilyl)propylamino]benzoyl]methanesulfonamide |
| 211 | 188 | N—[4-[10-(Trimethylsilyl)decylamino]-benzoyl]alanine |
| 212 | 188 | N—[4-[3-(Hexadecyldimethylsilyl)propylamino]benzoyl]alanine |
| 213 | 189 | N—[4-[9-(Trimethylsilyl)nonylamino]-benzoyl]benzamide |
| 214 | 189 | N—[4-[14-(Cyclohexyldimethylsilyl)-tetradecylamino]benzoyl]benzamide |
| 215 | 189 | N—[4-[11-(t-Butyldimethylsilyl)undecylamino]benzoyl]benzamide |
| 216 | 190 | N—(2,3-Dihydroxypropyl)-4-[7-(trimethylsilyl)heptylamino]benzamide |
| 217 | 190 | N—(2,3-Dihydroxypropyl)-4-[3-(trihexylsilyl)propylamino]benzamide |

TABLE VII-continued

The following benzamides are prepared from the corresponding carboxylic acids of Table IV (or activated derivatives thereof prepared by the methods of Examples 142-145) by the methods of Examples 183-190 as shown in the table.

| Example No. | Method of Example | Compound |
|---|---|---|
| 218 | 190 | N—(2,3-Dihydroxypropyl)-4-[14-(triethylsilyl)tetradecylamino]benzamide |
| 219 | 190 | N—(2,3-Dihydroxypropyl)-4-[11-[2-(3-cyclohexenyl)ethyldimethylsilyl]-undecylamino]benzamide |

EXAMPLE 220

Diethyl 4-[14-(trimethylsilyl)tetradecylamino]benzoylmalonate

A solution of 26.6 g. of diethyl malonate and 10 ml. of 1,2-dimethoxyethane is added to a suspension of 4.0 g. of sodium hydride in 1,2-dimethoxyethane under argon. A solution of 16.9 g. of 4-[14-(trimethylsilyl)tetradecylamino]benzoyl chloride hydrochloride in 1,2-dimethoxyethane is then added. The reaction mixture is refluxed for 4.5 hours, cooled, poured on ice, acidified, and extracted with ether. The ether solution is washed with water and saturated sodium chloride solution, dried with anhydrous sodium sulfate and evaporated to dryness. Addition of a small amount of ethanol to the residue gives a solid which is filtered and discarded. The ethanol filtrate is evaporated and the residue is recrystallized to yield the title product.

EXAMPLE 221 tert-Butyl ethyl 4-[14-(trimethylsilyl)tetradecylamino]benzoylmalonate

A solution of 14 g. of tert-butyl ethyl malonate in 5 ml. of 1,2-dimethoxyethane is added to a suspension of 2.0 g. of sodium hydride in 1,2-dimethoxyethane under argon. A solution of 8.4 g. of 4-[14-(trimethylsilyl)tetradecylamino]benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried with anhydrous sodium sulfate and evaporated to dryness. The residue is then recrystallized to yield the title compound.

EXAMPLE 222

Ethyl 4-[14-(trimethylsilyl)tetradecylamino]benzoylacetate

A solution of 3.0 g. of tert-butyl ethyl 4-[14-(trimethylsilyl)tetradecylamino]benzoylmalonate and 10 ml. of trifluoroacetic acid is warmed with stirring for 3 hours. The solution is poured onto ice and neutralized with potassium hydroxide. The resulting precipitate is collected by filtration, washed with water and dried. Recrystallization affords the product as a white solid.

EXAMPLE 223

4-[14-(Trimethylsilyl)tetradecylamino]benzoylacetic acid

Two grams of ethyl 4-[14-(trimethylsilyl)tetradecylamino]benzoylacetate is added to a solution of potassium hydroxide in 50 ml. of 1:9 water-ethanol. The reaction mixture is stirred for 24 hours at room temperature. Careful neutralization with sulfuric acid gives a precipitate which is filtered, washed with water, and dried to yield the product.

EXAMPLE 224

4'-[14-(Trimethylsilyl)tetradecylamino]-2-(methylsulfinyl)acetophenone

To a solution of 5.8 g. of dimethylsulfoxide, dried over sieves, and 50 ml. of tetrahydrofuran is slowly added 28 ml. of n-butyl lithium (2.42M in hexane). To this mixture is added 9.8 g. of methyl 4-[14-(trimethylsilyl)tetradecylamino]benzoate in 200 ml. of tetrahydrofuran. After two hours, the reaction mixture is poured onto ice, acidified with dilute hydrochloric acid and quickly extracted with chloroform. The chloroform extract is washed with water and saturated sodium chloride solution and dried with anhydrous sodium sulfate. Evaporation affords a solid which is washed with hexane. The white solid is dried in vacuo to yield the product.

EXAMPLE 225

4'-]14-(Trimethylsilyl)tetradecylamino]-2-(phenylsulfonyl)acetophenone

A solution of 864 mg. of sodium hydride and 5.3 g. of methylphenylsulfone in 20 ml. of 1,2-dimethoxyethane is stirred at 60° C. for one hour under an atmosphsere of argon. To this solution is then added a solution of 5.0 g. of methyl 4-[14-(trimethylsilyl)tetradecylamino]benzoate and 50 ml. of tetrahydrofuran and the reaction mixture is stirred at 60° C. for 1.5 hours. The mixture is cooled, poured onto ice, acidified with dilute hydrochloric acid to pH 3 and then extracted with chloroform. The organic layer is separated, washed three times with water and saturated sodium chloride solution, dried with anhydrous sodium sulfate and then evaporated to dryness. The crude solid is chromatographed on silica gel, eluting with methylene chloride to yield the product.

EXAMPLE 226

3-[4-[14-(Trimethylsilyl)tetradecylamino]benzoyl]-2,4-pentanedione

A solution of 14.2 g. of 2,4-pentanedione and 20 ml. of 1,2-dimethoxyethane is added to a suspension of 6.8 g. of sodium hydride in 110 ml. of 1,2-dimethoxyethane under argon. A solution of 14.0 g. of 4-[14-(trimethylsilyl)tetradecylamino]benzoyl chloride hydrochloride in 1,2-dimethoxyethane is then added. The reaction mixture is stirred at room temperature for 12 hours, cooled, poured on ice and extracted with ether. The ether solution is washed with water and saturated sodium chloride solution, dried with anhydrous sodium sulfate and evaporated. The residue is then chromatographed over silica gel to yield the product as a white solid.

EXAMPLE 227

3-[4-[14-(Trimethylsilyl)tetradecylamino]benzoyl]propionic acid

A mixture of 35 g. of 3-(4-acetamidobenzoyl)propionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The solid is collected and washed with cold methanol to yield methyl 3-(4-aminobenzoyl)-propionate as a white solid. A mixture of this solid, 8.0 g. of 14-(trimethylsilyl)tetradecyl bromide and 4.2 g. of potassium carbonate is stirred for 20 hours at 125° C. under nitrogen. The mixture is then cooled to 25° C. and 30 ml. of water is added. After stirring, the product is filtered and washed with water. Recrystallization affords methyl 3-[4-[14-(trimethylsilyl)tetradecylamino]-benzoyl]propionate as a white solid.

A solution of 5.4 g. of methyl 3-[4-[14-(trimethylsilyl)tetradecylamino]benzoyl]propionate is stirred with 5.4 g. of potassium hydroxide in 100 ml. of 95% ethanol for 3 hours at reflux. The reaction mixture is cooled, diluted with 50 ml. of ethanol and 100 ml. of water, and neutralized with hydrochloric acid. The solution is cooled to room temperature and filtered. The white solid is washed with 50% aqueous ethanol and dried. The product is recrystallized to yield 3-[4-[14-(trimethylsilyl)tetradecylamino]benzoyl]propionic acid as a white crystalline solid.

The following benzoyl analogs are prepared from the benzoic acids or benzoate esters of Tables III and IV (or activated derivatives thereof prepared by the methods of Examples 142–145) by the methods of Examples 220–227 as shown in the table.

| Example No. | Methods of Example | Compound |
| --- | --- | --- |
| 228 | 220 | Diethyl 4-[6-(trimethylsilyl)hexylamino]benzoylmalonate |
| 229 | 220 | Diethyl 4-[11-(tripropylsilyl)undecylamino]benzoylmalonate |
| 230 | 221 | t-Butyl ethyl 4-[9-(trimethylsilyl)nonylamino]benzoylmalonate |
| 231 | 221 | t-Butyl ethyl 4-[14-(pentyldimethylsilyl)tetradecylamino]benzoylmalonate |
| 232 | 221 | Ethyl 2-[4-[17-(trimethylsilyl)heptadecylamino]benzoyl]acetoacetate |
| 233 | 221 | Ethyl 2-[4-[3-(ethylhexylmethylsilyl)propylamino]benzoyl]acetoacetate |
| 234 | 222 | Ethyl 4-[18-(trimethylsilyl)octadecylamino]benzoylacetate |
| 235 | 222 | Ethyl 4-[11-(t-butyldimethylsilyl)undecylamino]benzoylacetate |
| 236 | 223 | 4-[18-(Trimethylsilyl)octadecylamino]benzoylacetic acid |
| 237 | 223 | 4-[11-(t-Butyldimethylsilyl)undecylamino]benzoylacetic acid |
| 238 | 224 | 4'-[11-(Trimethylsilyl)undecylamino]-2-(methylsulfinyl)acetophenone |
| 239 | 224 | 4'-[3-(Pentyldimethylsilyl)propylamino]-2-(methylsulfinyl)acetophenone |
| 240 | 224 | 4'-[14-(Cyclohexyldimethylsilyl)tetradecylamino]-2-(phenylsulfinyl)acetophenone |
| 241 | 224 | 4'-[11-(Tripropylsilyl)undecylamino]-2-(phenylsulfinyl)acetophenone |
| 242 | 225 | 4'-[3-(Pentyldimethylsilyl)propylamino]-2-(phenylsulfonyl)acetophenone |
| 243 | 225 | 4'-[11-(Ethylhexylmethylsilyl)undecylamino]-2-(phenylsulfonyl)acetophenone |
| 244 | 226 | 3-[4-[13-(Trimethylsilyl)tetradecylamino]benzoyl]2,4-pentanedione |
| 245 | 226 | 3-[4-[11-(t-Butyldimethylsilyl)undecylamino]benzoyl]2,4-pentanedione |
| 246 | 226 | 3-[4-[3-(Pentyldimethylsilyl)propylamino]benzoyl]2,4-pentanedione |
| 247 | 227 | 3-[4-[5-(Trimethylsilyl)pentylamino]benzoyl]propionic acid |
| 248 | 227 | 3-[4-[14-(Cyclohexyldimethylsilyl)undecylamino]benzoyl]propionic acid |
| 249 | 227 | 3-[4-[14-(Ethylhexylmethylsilyl)tetradecylamino]benzoyl]propionic acid |

EXAMPLE 250

4-[14-(Trimethylsilyl)tetradecylamino]phenylacetic acid

A solution of 8.2 g. of 4-aminophenylacetic acid, 150 ml. of absolute ethanol, and 3 ml. of boron trifluoride etherate is heated to reflux for 15 hours. The solution is concentrated by distillation and then evaporated to dryness in vacuo. The residue is dissolved in ethyl ether, washed with aqueous sodium bicarbonate, dried, and evaporated to yield ethyl 4-aminophenylacetate. A mixture of 5.0 g. of this amine, 9.7 g. of 14-(trimethylsilyl)tetradecyl bromide, 4.2 g. of anhydrous potassium carbonate and 40 ml. of hexamethylphosphoramide is heated at 80° C. for 7 hours. The mixture is then cooled, diluted with water, and extracted with ethyl ether. The ether extracts are washed with water, dried and evaporated. The residue is recrystallized yielding ethyl 4-[14-(trimethylsilyl)tetradecylamino]phenylacetate. A mixture of 6.0 g. of this ester, 7.0 g. of potassium hydroxide and 100 ml. of ethanol-water is heated to reflux for 4 hours. While hot, the mixture is adjusted to pH 7 with concentrated hydrochloric acid.. The mixture is diluted with water, cooled and filtered. Recrystallization of the precipitate yields the title product as a white solid.

EXAMPLE 251

4-[14-(Trimethylsilyl)tetradecylamino]hydrocinnamic acid

A mixture of 5.0 g. of 4-nitrocinnamic acid and 100 mg. of 10% palladium-on-carbon in 200 ml. of ethanol containing 5 drops of 5.5N ethanolic hydrogen chloride is treated with hydrogen in a Parr apparatus at room temperature for 3 hours. The mixture is then filtered through celite and the filtrate is evaporated, affording 4-aminohydrocinnamic acid.

A solution of 5.0 g. 4-aminohydrocinnamic acid in 50 ml. of absolute ethanol containing 8 ml. of boron trifluoride etherate is heated to reflux for 48 hours. The solution is then cooled, poured into 5% aqueous sodium carbonate, and extracted with methylene chloride. Evaporation of the organic extracts yields ethyl 4-aminohydrocinnamate.

In a manner directly analogous to that described in Example 6, ethyl 4-aminohydrocinnamate is alkylated with 14-(trimethylsilyl)tetradecyl bromide to form ethyl 4-[14-(trimethylsilyl)tetradecylamino]hydrocinnamate. Subsequently, in a manner directly analogous to that described in Example 9, ethyl 4-[14-(trimethylsilyl)tetradecylamino]hydrocinnamate is hydrolyzed to 4-[14-(trimethylsilyl)tetradecylamino]hydrocinnamic acid.

EXAMPLE 252

4-[14-(Trimethylsilyl)tetradecylamino]cinnamic acid

A mixture of 5.0 g. ethyl 4-aminocinnamate, 9.14 g. of 14-(trimethylsilyl)tetradecyl bromide and 3.6 g. of powdered anhydrous potassium carbonate in hexamethylphosphoramide is heated for 20 hours at 60° C. The mixture is then cooled, diluted with water and extracted with ether. The combined ether extracts are dried, filtered and evaporated to provide ethyl 4-[14-(trimethylsilyl)tetradecylamino]cinnamate. The ester is hydrolyzed with sodium hydroxide in a 1:9 water:ethanol solution at steam bath temperature for 10 hours. The hot solution is then acidified with acetic acid, cooled and filtered and the solid is washed with water. Recrystallization from chloroform yields the title product as a white solid.

EXAMPLE 253

4-[14-(Trimethylsilyl)tetradecylamino]phenylpropiolic acid

A sample of 50 g. of ethyl 4-aminocinnamate is dissolved in 500 ml. of ethyl ether and a solution of 28 g. of trifluoroacetic anhydride in 30 ml. of ether is added dropwise. When the addition is compelte, the reaction is allowed to stir for another hour. The mixture is then diluted with hexane and filtered, providing ethyl 4-trifluoroacetamidocinnamate.

A solution of 40 g. of ethyl 4-trifluoroacetamido cinnamate in 200 ml. of carbon tetrachloride is cooled in ice. Bromine (28 g.) is added dropwise, the reaction is allowed to stir for one additional hour and then the solvent is evaporated. The crystalline residue is the dibromo ester.

A solution of 11.4 g. of potassium hydroxide in 300 ml. of 95% ethanol is cooled to 40° C. and 20 g. of the crude dibromo ester above is added. After 30 minutes, the reaction is heated to reflux for five hours. The solution is then cooled and filtered. The filtrate is treated with acetic acid until the solution is neutral to litmus, then evaporated, chilled and filtered, to yield 4-aminophenylpropiolic acid.

The 4-aminophenylpropiolic acid is converted to 4-[14-(trimethylsilyl)tetradecylamino]phenylpropiolic acid in the manner of Example 250.

The following carboxylic acids are prepared by alkylation of the corresponding 4-aminophenyl carboxylate esters with the appropriate trialkylsilylalkyl halide, trifluoromethanesulfonate, or methanesulfonate followed by hydrolysis using the methods of Examples 250-253 as shown in the table.

| Example No. | Method of Example | Compound |
|---|---|---|
| 254 | 250 | 4-[7-(Trimethylsilyl)heptylamino]phenylacetic acid |
| 255 | 250 | 4-[14-(t-Butyldimethylsilyl)tetradecylamino]phenylacetic acid |
| 256 | 250 | 4-[11-(Pentyldimethylsilyl)undecylamino]phenylacetic acid |
| 257 | 250 | 4-[3-[2-(3-Cyclohexenyl)ethyldimethylsilyl]propylamino]phenylacetic acid |
| 258 | 251 | 4-[8-(Trimethylsilyl)octylamino]hydrocinnamic acid |
| 259 | 251 | 4-[11-(Hexyldimethylsilyl)undecylamino]hydrocinnamic acid |
| 260 | 251 | 4-[14-(Trimethylsilyl)tetradecylamino]hydrocinnamic acid |
| 261 | 251 | 4-[3-(Ethylhexylmethylsilyl)propylamino]hydrocinnamic acid |
| 262 | 252 | 4-[19-(Trimethylsilyl)nonadecylamino]cinnamic acid |
| 263 | 252 | 4-[11-(Trihexylsilyl)undecylamino]cinnamic acid |
| 264 | 252 | 4-[3-(Pentyldimethyl)propylamino]cinnamic acid |
| 265 | 252 | 4-[14-(Ethylhexylmethylsilyl)tetradecylamino]cinnamic acid |
| 266 | 252 | 4-[14-(Ethylhexylmethylsilyl)tetradecylamino]cinnamic acid |
| 267 | 253 | 4-[11-(t-Butyldimethylsilyl)undecylamino]phenylpropiolic acid |
| 268 | 253 | 4-[19-(Trihexylsilyl)nonadecylamino]phenylpropiolic acid |
| 269 | 253 | 4-[14-(Pentyldimethylsilyl)tetradecylamino]phenylpropiolic acid |

We claim:

1. A compound of the formula:

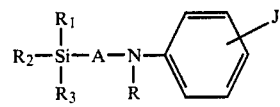

wherein, A is selected from the group consisting of a saturated, straight-chain alkylene moiety of 3-20 carbon atoms; a saturated, branched alkylene moiety of 3-20 carbon atoms; an unsaturated, straight-chain alkylene moiety of 3-20 carbon atoms; an unsaturated, and branched alkylene moiety of 3-20 carbon atoms;

$R_1$, $R_2$, and $R_3$ are the same or different and are independently selected from the group consisting of $C_1$–$C_6$ alkyl, $C_2$–$C_6$ alkenyl, $C_2$–$C_6$ alkynyl, $C_4$–$C_7$ cycloalkyl, and $C_4$–$C_{20}$ cycloalkylalkyl;

R is selected from the group consisting of hydrogen, methyl, carboxymethyl, acetyl, succinyl, and sodium sulfo-methyl; and (a) J is

Z being selected from the group consisting of hydrogen, $C_1$–$C_4$ alkyl, hydroxy, $C_1$–$C_4$ alkoxy, 2,3-dihydroxypropyl, alkyloxy, 2,3-epoxypropyl, benzoyloxy, phenoxy, 3-pyridyloxy, pyridylmethoxy, tetrahydropyranyloxy, amino, ($C_1$–$C_4$ alkyl)amino, di($C_1$–$C_4$ alkyl)amino, allylamino, propargylamino, 2-sulfoethylamino, ($C_1$–$C_4$-alkanoyl)amino, benzoylamino, ($C_1$–$C_4$-alkanesulfonyl)amino, benzenesulfonylamino, toluenesulfonylamino;

(b) J is selected from the group consisting of (carboxy)-$C_1$–$C_4$-alkyl, (carboxy)-$C_2$–$C_4$-alkenyl, (carboxy)-$C_2$–$C_4$-alkylnyl, ($C_1$–$C_4$-carboalkoxy)-$C_1$–$C_4$-alkyl, ($C_1$–$C_4$-carboalkoxy)-$C_2$–$C_4$-alkenyl, ($C_1$–$C_4$-carboalkoxy)-$C_2$–$C_4$-alkynyl; and the pharmaceutically acceptable, non-toxic, acid-addition and cationic salts thereof.

2. A compound as recited in claim 1 wherein; R is hydrogen and J is

3. A compound as recited in claim 2 wherein; A is selected from the group consisting of a saturated alkylene moiety of 3-20 carbon atoms and an unsaturated moiety of 3-20 carbon atoms.

4. A compound as recited in claim 2 wherein: A is a saturated alkylene moiety of 3-20 carbon atoms; and $R_1$, $R_2$, and $R_3$ are independently selected from the group consisting of $C_1$-$C_6$ alkyl, $C_3$-$C_6$ cycloalkyl, and $C_3$-$C_6$ cycloalkenyl.

5. A compound as recited in claim 4 wherein; Z is selected from the group consisting of hydroxy and $C_1$-$C_4$ alkoxy; and $R_1$, $R_2$, and $R_3$ are all methyl, and the pharmaceutically acceptable, non-toxic, acid addition and cationic salts thereof.

6. The compound ethyl 4-[11-(trimethylsilyl)undecylamino]benzoate.

7. The compound 4-[11-(Trimethylsilyl)undecylamino]benzoic acid.

8. The compound sodium 4-[11-(trimethylsilyl)undecylamino]benzoate.

9. The compound ethyl 4-[14-(trimethylsilyl)tetradecylamino]benzoate.

10. The compound 4-[14-(trimethylsilyl)tetradecylamino]benzoic acid.

11. The compound sodium 4-[14-(trimethylsilyl)tetradecylamino]benzoate.

12. The compound ethyl 4-[3-(trimethylsilyl)propylamino]benzoate.

13. The compound 4-[3-(trimethylsilyl)propylamino]benzoic acid.

14. The compound sodium 4-[3-(trimethylsilyl)propylamino]benzoate.

15. A method of treating atherosclerosis in mammals in need of such treatment which comprises administering to said mammal an effective amount of a compound as recited in claim 1, 2, 3, 4, or 5.

16. A method of treating hyperlipidemia in mammals in need of such treatment which comprises administering to said mammal an effective amount of a compound as recited in claim 1, 2, 3, 4, or 5.

17. A method of reducing the cholesterol content of the arterial walls of mammals in need of such treatment which comprises administering to said mammal an effective amount of a compound as recited in claim 1, 2, 3, 4, or 5.

18. A method of inhibiting atherosclerotic lesion development in mammals in need of such treatment which comprises administering to said mammal an effective amount of a compound as recited in claim 1, 2, 3, 4, or 5.

19. A pharmaceutical composition which comprises an effective antiatherosclerotic amount of a compound as recited in claim 1, 2, 3, 4, or 5 in association with a pharmaceutically acceptable carrier.

* * * * *